United States Patent
Trova et al.

[11] Patent Number: 5,908,840
[45] Date of Patent: *Jun. 1, 1999

[54] HETERO-BIARYL-PYRIDOQUINAZOLINONE DERIVATIVES AS ANTI-CANCER AGENTS

[75] Inventors: Michael P. Trova, Schenectady; Nan Zhang, Valley Cottage, both of N.Y.

[73] Assignee: American Cyanamid Company, Madison, N.J.

[21] Appl. No.: 08/965,217

[22] Filed: Nov. 6, 1997

Related U.S. Application Data

[60] Provisional application No. 08/031,781, Nov. 26, 1996.

[51] Int. Cl.$^6$ .................. A61K 31/505; A61K 31/55; C07D 471/04
[52] U.S. Cl. .................. 514/212; 514/267; 540/600; 544/252
[58] Field of Search .................. 544/252; 540/600; 514/267, 212

[56] References Cited

U.S. PATENT DOCUMENTS

| | | | |
|---|---|---|---|
| 4,033,961 | 7/1977 | Schwender et al. | 544/247 |
| 4,104,389 | 8/1978 | Schwender et al. | 514/267 |
| 4,348,396 | 9/1982 | Kierstead et al. | 514/267 |

OTHER PUBLICATIONS

Denny et al., Structure–activity relationships for the mutagenic activity of tricyclic intercalating agents in *Selmonella typhimurium*, Mutation Research, 232(1990) p. 233.

Ebeid et al., Synthesis and Antitumor Activity of Some N(p–Substituted Sulfamoylphenyl) Acridone–4–Carboxamides and N(p–substituted Sulfamoylphenyl)–11–oxo–11 H–Pyrido[2,1–b] Quinazoline–6–Carboxamides, Egypt.J.Pharm Sci., vol. 33, No. 1–2, pp. 293–303 (1992).

*Primary Examiner*—Emily Bernhardt
*Attorney, Agent, or Firm*—Arnold S. Milowsky

[57] ABSTRACT

This invention provides a compound having the formula:

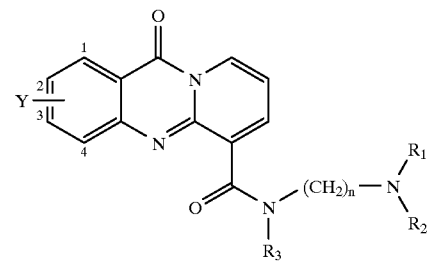

wherein:

(A) n=2–4;
(B) $R_1$ and $R_2$ are the same or different and selected from the group consisting of H, ($C_1$–$C_3$) alkyl, —$CH_2CH_2OH$, —$CH_2CH_2NH_2$, and —$CH_2CH_2N(CH_3)_2$ or $R_1$ and $R_2$ are alkyl moieties which are taken together to form a 4- to 7- membered ring;
(C) $R_3$ is selected from the group consisting of H, —$CH_3$, —$CH_2CH_3$, and —$CH_2CH_2NH_2$;
(D) Y is a heterocyclic radical having 5–14 atoms, located at the 2- or 3- position of the pyridoquinazolinone nucleus, in which 1–3 of the heterocyclic ring atoms are independently nitrogen, oxygen, or sulfur; wherein Y may be optionally mono-, di-, or tri- substituted with —$OR_4$, —$NR_5R_6$, —$CO_2H$, —$CO_2R_4$, or phenyl;
$R_4$ is H or ($C_1$–C4) straight-chain alkyl;
$R_5$ and $R_6$ are the same or different and are selected from the group consisting of H, ($C_1$–$C_4$) straight-chain alkyl, —$CH_2CH_2OH$, —$CH_2CH_2NH_2$, and —$CH_2CH_2N(CH_3)_2$ or $R_5$ and $R_6$ are alkyl moieties which are taken together to form a 4–7 membered ring;

or a pharmaceutically acceptable salt thereof which is useful as an antineoplastic agent.

11 Claims, No Drawings

HETERO-BIARYL-PYRIDOQUINAZOLINONE DERIVATIVES AS ANTI-CANCER AGENTS

BACKGROUND OF THE INVENTION

This application claims the benefit of U.S. Provisional Application No. 60/031,781, filed Nov. 26, 1996.

Most of DNA intercalating anti-tumor drugs have a common structure: a tri- or tetracyclic chromophore with one or two flexible side chains. Denny et. al. reported synthesis and biological activity of N-[2-(dimethylamino)ethyl]-11-oxo-11H-pyrido[2,1-b]quinalzoline-6-carboxamide (I) as a potential anti-cancer agent. [Mutation Research 232: 233 (1990)]. In these reports, they claim that this compound showed some in vitro activity and mutagenic activity, but was inactive in a P388 mouse model. Ebeid et. al. reported synthesis of N(p-substituted sulfamoylphenyl)-11-oxo-11-H-pyrido[2,1-b]quinalzoline-6-carboxamides (II). Only one compound showed in vitro activity. [Egypt. J. Pharm. Sci. 33: 293 (1992)].

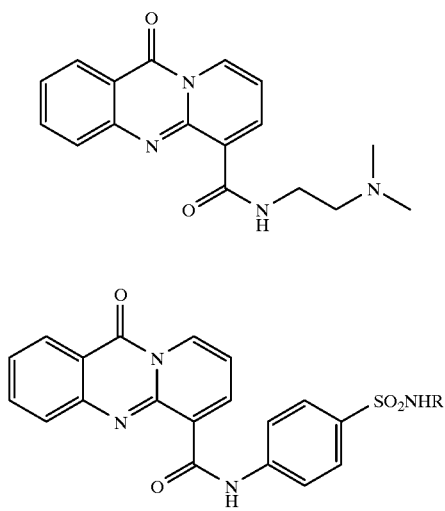

Substituted 11-oxo-11H-pyrido[2,1-b]quinalzolines have been patented as anti allergy agents. Neither these patents nor the references cited above, cover any biaryl compounds described in this application. [U.S. Pat. Nos. 4,033,961, 4,104,389, and 4,384,396].

BRIEF SUMMARY OF THE INVENTION

This invention provides compounds having the formula:

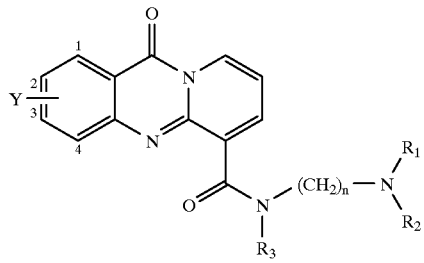

wherein:
(A) n=2–4;
(B) $R_1$ and $R_2$ are the same or different and selected from the group consisting of H, $(C_1-C_3)$ alkyl, —$CH_2CH_2OH$, —$CH_2CH_2NH_2$, and —$CH_2CH_2N(CH_3)_2$ or $R_1$ and $R_2$ are alkyl moieties which are taken together to form a 4- to 7- membered ring;
(C) $R_3$ is selected from the group consisting of H, —$CH_3$, —$CH_2CH_3$, and —$CH_2CH_2NH_2$;
(D) Y is a heterocyclic radical having 5–14 atoms, located at the 2- or 3- position of the pyridoquinazolinone nucleus, in which 1–3 of the heterocyclic ring atoms are independendy nitrogen, oxygen, or sulfur; wherein Y may be optionally mono-, di-, or tri- substituted with —$OR_4$, —$NR_5R_6$, —$CO_2H$, —$CO_2R_4$, or phenyl;
$R_4$ is H or $(C_1-C_4)$ straight-chain alkyl;
$R_5$ and $R_6$ are the same or different and are selected from the group consisting of H, $(C_1-C_4)$ straight-chain alkyl, —$CH_2CH_2OH$, —$CH_2CH_2NH_2$, and —$CH_2CH_2N(CH_3)_2$ or $R_5$ and $R_6$ are alkyl moieties which are taken together to form a 4–7 membered ring;
or a pharmaceutically acceptable salt thereof.

A preferred embodiment of the present invention is provided by compounds having the formula:

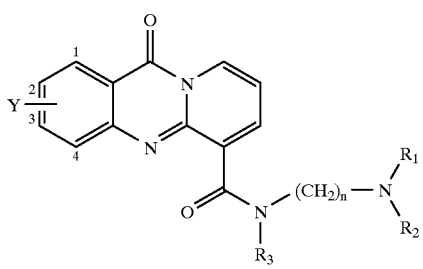

wherein:
(A) n=2–4;
(B) $R_1$ and $R_2$ are the same or different and selected from the group consisting of H, $(C_1-C_3)$ alkyl, —$CH_2CH_2OH$, —$CH_2CH_2NH_2$, and —$CH_2CH_2N(CH_3)_2$ or $R_1$ and $R_2$ are alkyl moieties which are taken together to form a 4- to 7- membered ring;
(C) $R_3$ is selected from the group consisting of H, —$CH_3$, —$CH_2CH_3$, and —$CH_2CH_2NH_2$;
(D) Y is located at the 2- or 3- position of the pyridoquinazolinone nucleus and is a radical selected from the group consisting of 2-thienyl, 3-thienyl, 2-furyl, 3-furyl, 2-pyrrolyl, 3-pyrrolyl, 2-pyridinyl, 3-pyridinyl, 4-pyridinyl, 2-pyrimidinyl, 4-pyrimidinyl, 5-pyrimidinyl, 2-imidazolyl, 4-imidazolyl, 2-pyrazinyl, 2-oxazolyl, 4-oxazolyl, 2-thiazolyl, 4-thiazolyl, 2-benzothienyl, 3-benzothienyl, 4-benzothienyl, 5-benzothienyl, 6-benzothienyl, 7-benzothienyl, 2-benzofuranyl, 3-benzofuranyl, 4-benzofuranyl, 5-benzofuranyl, 6-benzofuranyl, 7-benzofuranyl, 2-indolyl, 3-indolyl, 4-indolyl, 5-indolyl, 6-indolyl, 7-indolyl, 2-quinolinyl, 3-quinolinyl, 4-quinolinyl, 5-quinolinyl, 6-quinolinyl, 7-quinolinyl, 8-quinolinyl, 1-isoquinolinyl, 3-isoquinolinyl, 4-isoquinolinyl, 5-isoquinolinyl, 6-isoquinolinyl, 7-isoquinolinyl, 8-isoquinolinyl, 2-quinazolinyl, 4-quinazolinyl, 5-quinazolinyl, 6-quinazolinyl, 7-quinazolinyl, and 8-quinazolinyl, wherein Y may be optionally mono-, di-, and tri- substituted with $OR_4$, $-NR_5R_6$, $-CO_2H$, $-CO_2R_4$, or phenyl;

$R_4$ is H or $(C_1-C_4)$ straight-chain alkyl;

$R_5$ and $R_6$ are the same or different and are selected from the group consisting of H, $(C_1-C_4)$ straight-chain alkyl, $-CH_2CH_2OH$, $-CH_2CH_2NH_2$, and $-CH_2CH_2N(CH_3)_2$, or $R_5$ and $R_6$ are alkyl moieties which are taken together to form a 4–7 membered ring;

or a pharmaceutically acceptable salt thereof.

A more preferred embodiment of the present invention is provided by compounds having the formula:

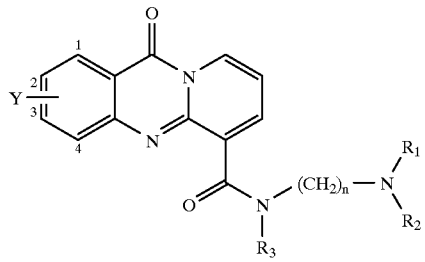

1 wherein:
(A) n=2;
(B) $R_1$ and $R_2$ are both $-CH_3$, or $R_1$ and $R_2$ are alkyl moieties which are taken together to form a pyrrolidine ring;
(C) $R_3$ is H;
(D) Y is located at the 2- or 3- position of the pyridoquinazolinone nucleus and is a radical selected from the group consisting of 3-pyridinyl, 4-pyridinyl, and 3-quinolinyl;

or a pharmaceutically acceptable salt thereof.

DETAILED DESCRIPTION OF THE INVENTION

The preparation of pyridoquinazolinones of this invention containing Y attached to the 2-position of the nucleus is described below in Flowsheet A. Condensation of 2-amino-5-iodobenzoic acid (2) with 2-chloronicotinic acid (3) in a polar protic solvent such as ethanol or aqueous ethanol in the presence of a catalytic amount of a mineral acid such as hydrochloric acid at temperatures in excess of 80° C. provides heterocycle 4. The carboxylic acid group within 4 can be converted into an amide 6 by reaction with amine 5 in the presence of a coupling agent, such as benzotriazol-1-yloxytris(dimethylamino)phosphonium hexafluorophosphate (BOP reagent), a base, such as N,N-diisopropylethylamine (Hünigs base) and an inert solvent such as dichloromethane. Heterobiaryl compound 7 is prepared by a palladium (0) mediated coupling reaction of 6 with heteroarylboronic acid 8, a catalytic amount of (triphenylphosphine)palladium (0), a base such as sodium carbonate, in water, and an inert solvent such as toluene at or below reflux temperature.

An alternative approach to prepare amide 6, involves first transformation of acid 4 into its acid chloride 9 by reaction 4 with oxalyl chloride, a catalytic amount of dimethylformamide, in an inert solvent such as dichloromethane. Acid chloride 9 is reacted with amine 5 in the presence of a base, such as triethylamine in an inert solvent, such as dichloromethane to give amide 6.

An alternative approach to heterobiaryl 7 is reaction of iodide 6 with heteroaryltin derivatives 10 in the presence of palladium (0), such as tetrakis(triphenylphosphine)palladium (0), in an inert solvent such as toluene, at or below the reflux temperature.

The preparation of pyridoquinazolinones of this invention containing Y attached to the 3-position of the nucleus is described in Flowsheet B wherein n, $R_1$, $R_2$, $R_3$, and Y are described above.

4-Bromophthalic anhydride 11 is reacted with sodium methoxide in a solvent such as methanol, at or above ambient temperature, to provide a mixture of two esters 12 and 13. The mixture of two esters may be separated by conventional means such as chromatography, recrystallization or distillation. Alternatively, the mixture of esters 12 and 13 is allowed to react with diphenylphosphoryl azide ((PhO)$_2$P(O)N$_3$) in an inert solvent, such as toluene, at a temperature between 23°–150° C., followed by hydrolysis with aqueous acetone to provide a mixture of amines 14 and 15. The amines are readily separable from one another by chromatography, recrystallization or distillation.

Amine 14 is allowed to undergo condensation with 2-chloronicotinic acid (3) in a polar protic solvent such as ethanol, methanol, or aqueous ethanol in the presence of a catalytic amount of mineral acid such as hydrochloric acid at temperatures in excess of 80° C. to provide heterocycle 16. The carboxylic acid group within 16 can be converted into an amide 17 by reaction with amine 5 in the presence of a coupling agent, such as benzotriazol-1-yloxytris(dimethylamino)phosphonium hexafluorophosphate (BOP reagent), a base, such as N,N-diisopropylethylamine (Hünig's base) and an inert solvent such as dichloromethane.

Heterobiaryl compound 18 is prepared by a palladium (0) mediated coupling reaction of 6 with heteroarylboric acid 8, a catalytic amount of tetrakis(triphenylphosphine)palladium (0), a base such as sodium carbonate, in water, and an inert solvent such as toluene at or below reflux temperature.

An alternative approach to prepare amide 17 involves first transformation of acid 16 into its acid chloride 19 by reaction of 16 with oxalyl chloride, a catalytic amount of dimethylformamide, in a inert solvent such as dichloromethane. Acid chloride 19 is reacted with amine 5 in the presence of a base, such as triethylamine in an inert solvent, such as dichloromethane to give amide 17.

An alternative approach to heterobiaryl 18 is reaction of bromide 17 with heteroaryltin derivatives 10 in the presence of palladium (0), such as tetrakis(triphenylphosphine)palladium (0), in an inert solvent such as toluene, at or below the reflux temperature.

Flowsheet A
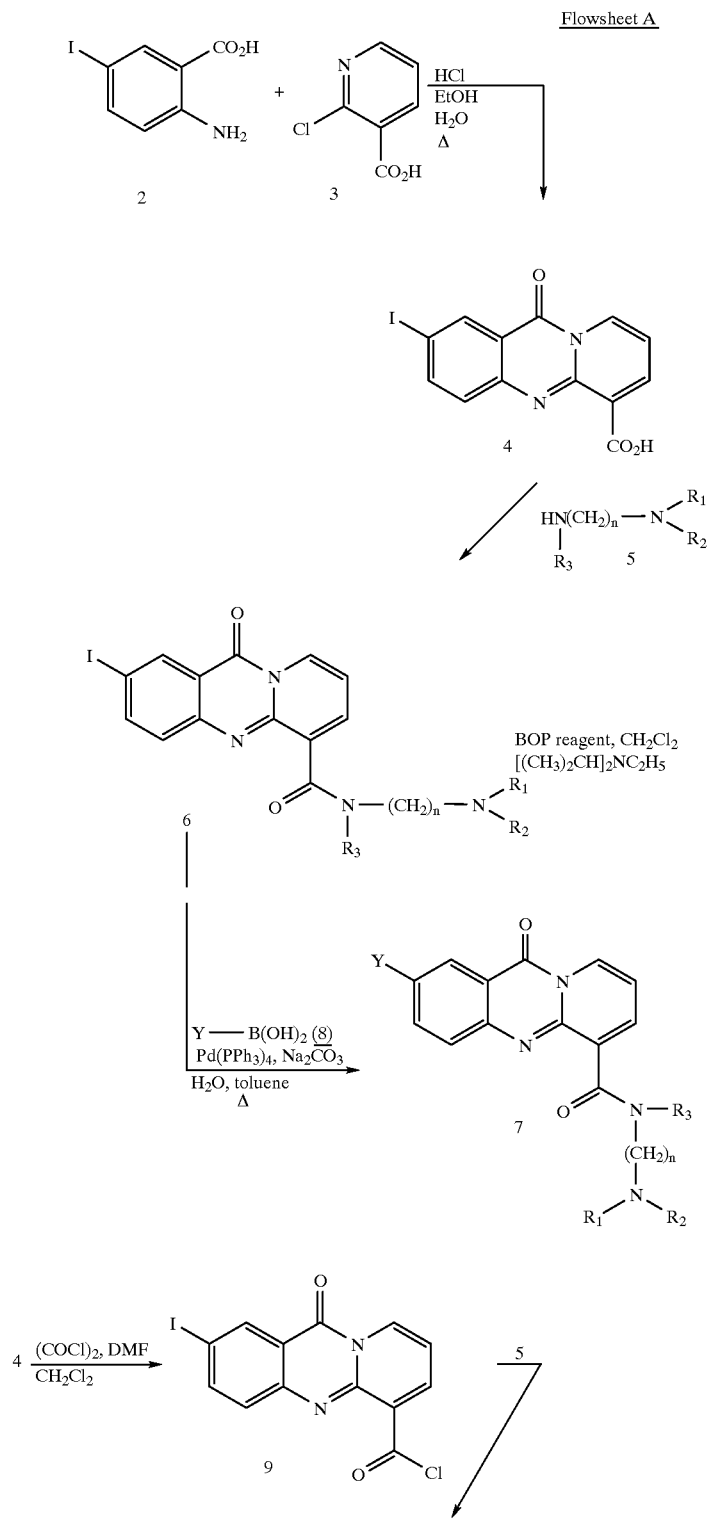

-continued
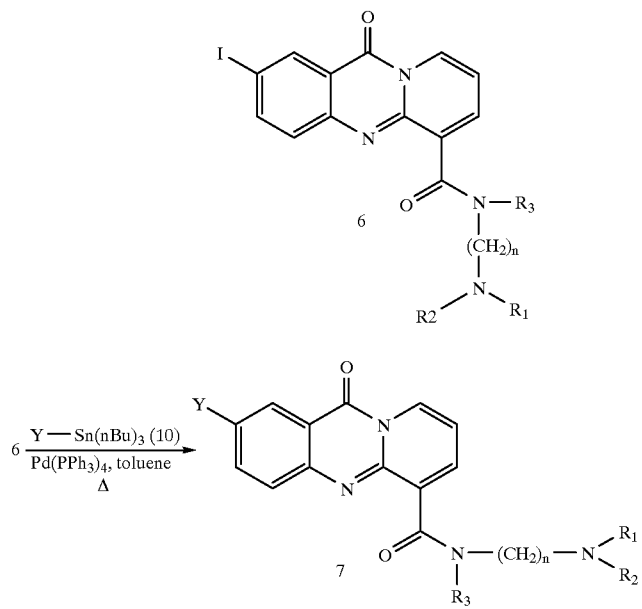
Flowsheet B
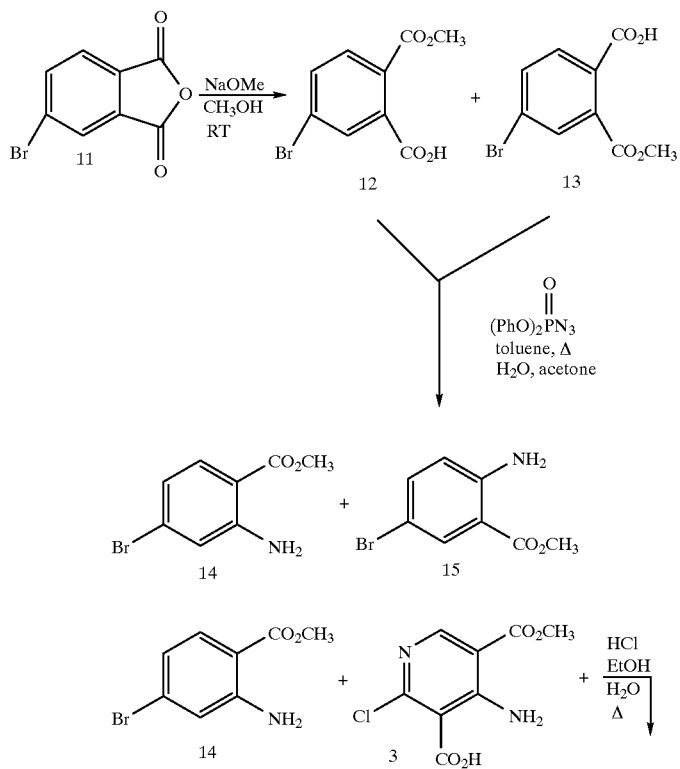

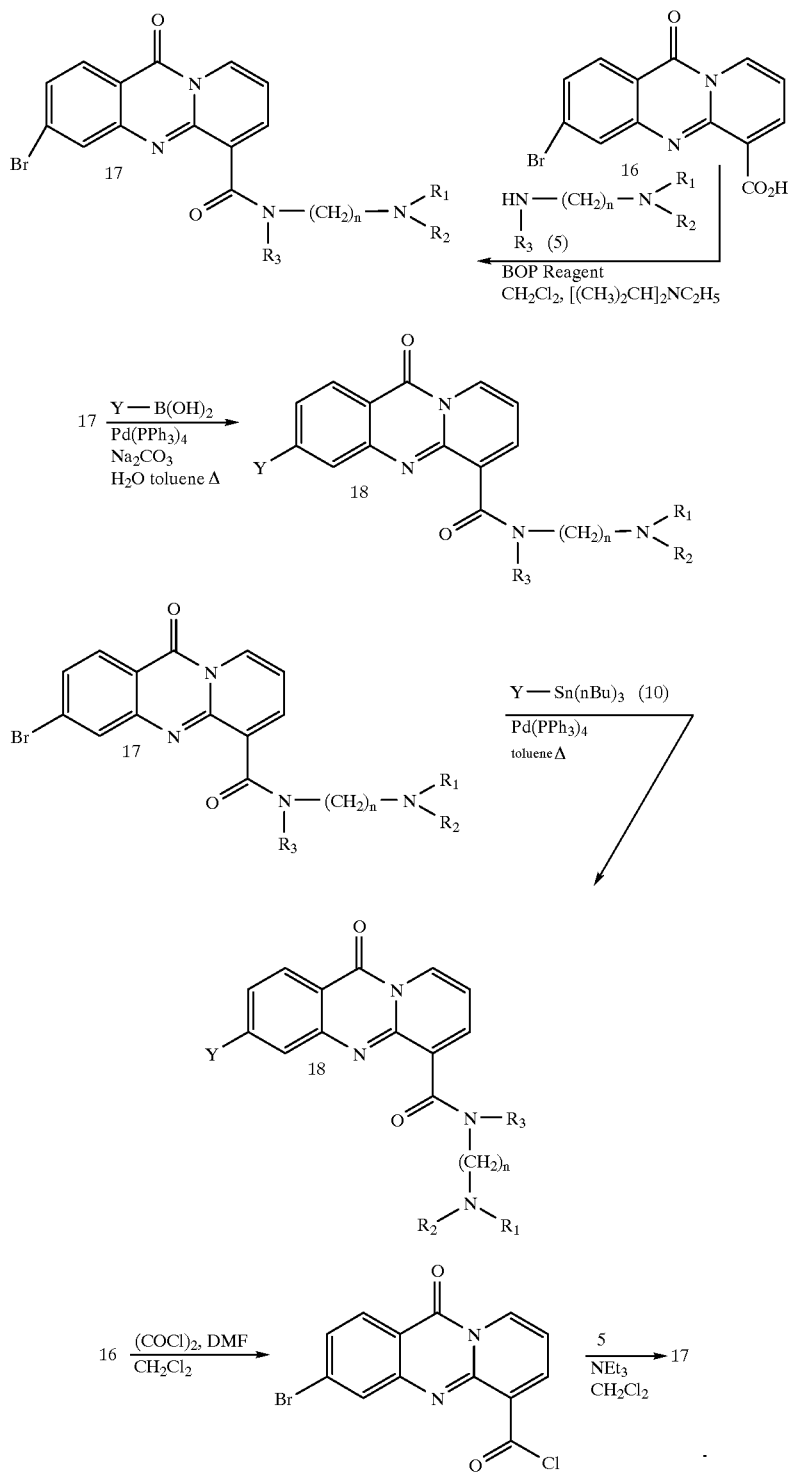

The preparation of the compounds of this invention encompassed by formulas 8 and 10 is described below in Flowsheet C wherein Y is defined above, and Z is selected from n-Bu, sec-Bu, and t-Bu.

Heteroaryl bromide 20 is allowed to undergo metal-halogen exchange with an alkyllithium Z-Li in an inert solvent, such as ether at a temperature between −100° C. to room temperature. The resulting anion is allowed to react with trimethyl borate (B(OMe)$_3$), followed by an acidic work-up to provide 8.

The above anions can also be reacted with tributyltin chloride ((nBu)$_3$SnCl) to provide heteroaryltin derivatives 10.

An alternative approach to heteroaryltin derivatives 10 is reaction of bromide 20 with bis(tributyltin) in the presence of palladium (0), such as tetrakis(triphenylphosphine)

palladium (0), in an inert solvent such as toluene, at or below the reflux temperature.

Flowsheet C

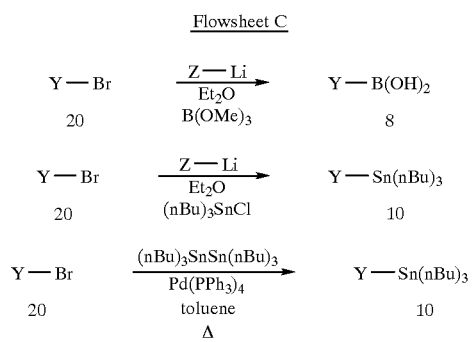

The pharmaceutically acceptable salts are those derived from pharmaceutically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The compounds of this invention are useful as antineoplastic agents as demonstrated by the results obtained for representative compounds of this invention in the following standard pharmacological test procedures.

Description of the Two Cell Line Test Procedure

A2780 S and A2780 DDP cells [Biochemical and Molecular Properties of Cisplatin-resistant A2780 Cells Grown in Folinic Acid; Y. Lu, J. Hnan, and K. Scanlon, *J. Biol. Chem.*, 263, 4891–4894, 1988.] are grown in RPMI 1640 medium containing 5% fetal calf serum, 50 μg/ml streptomycin, 50 units/ml penicillin, 50 82 g/ml gentamycin, 0.03% L-glutamine, 1 nM estradiol, 1 nM testosterone, 5 μg/ml insulin, 5 μg/ml transferrin, and 5 ng/ml selenous acid, at 37° C., in a humidified atmosphere, containing 5% $CO_2$. Experiments are done in the same media.

Cells are plated at the concentration of $5\times10^4$/ml on Day 0 of the experiment. On Day one cells are fixed with trichloroacetic acid and 5 ten-fold dilutions of tested compounds are added, in duplicates, to the remaining cells. On Day 3 (48 hours exposure to drugs) all cells are fixed with trichloroacetic acid, stained with 0.4% sulforhodamine B, and absorbency is read at 520 nm. The $IC_{50}$ (concentration causing 50% inhibition) are determined for each drug.

Murine Tumor Standard Pharmacological Test Procedures

Murine P388 Leukemia $CD2F_1$ mice are injected i.p. with $1\times10^6$ tumor cells on Day 0 of the test. Drugs are administered i.p. on Days 1, 5, and 9 after the tumor implantation. Positive drug response is indicated by a more than 25% increase in the mean life span (% ILS), relative to placebo treated controls. Drugs are considered to be toxic when the mean life span of the drug treated animals is more than 15% shorter than placebo treated controls.

Murine Colon 26 Advanced, Metastatic Tumor $CD2F_1$ mice are injected i.p. with $5\times10^5$ tumor cells on Day 0 of the test. Drugs are administered i.p. on Days 5, 9, and 13 after the tumor implantation. Positive drug response is indicated by a more than 25% increase in the mean life span (% ILS), relative to placebo treated controls. Drugs are considered to be toxic when the mean life span of the drug treated animals is more than 15% shorter than placebo treated controls.

Human Tumor Xenograft Model

Human tumor fragments are implanted s.c. in athymic nude mice. Tumors are allowed to grow until they attain a mass of 100–150 mgs. At Day 0 of the test, mice are placed into treatment groups such that mice in each group have approximately the same size tumors (tumor staging). Drugs are administered i.p. on Days 1, 5, and 9. Each mouse tumor mass is determined every 7 days, until Day 28, using caliper measurements of tumor length and width. Mean tumor mass for each group of animals is then calculated and the relative tumor growth determined. The relative tumor growth is defined as a ratio of the tumor mass on a given day to a tumor mass on Day 0. Calculation of % T/C (the relative tumor growth of treated group divided by the relative tumor growth of placebo group, multiplied by 100) is made for each day of measurement. A positive drug response is indicated by a % T/C value below 60%, and a p value in the Student t-test of less than 0.05. More than 20% deaths in the group related to the drug administration indicate toxicity.

TABLE 1

In Vitro Cytotoxicity Results in Two Cancer Cell Lines. A2780 DDP and A2780 S Lines

| Example No. | $IC_{50}$ (μg/ml) A2780 S | $IC_{50}$ (μg/ml) A2780 DDP |
|---|---|---|
| 15 | 0.60 | 0.70 |
| 16 | 7.00 | 8.60 |
| 10 | 4.50 | 5.30 |
| 06 | 0.90 | 5.00 |
| 07 | 0.70 | 5.60 |
| 08 | 0.80 | 3.70 |

TABLE 2

In Vivo Murine Tumor Results

| Example No. | Dose (mg/kg) | Treatment schedule (d) | % ILS | Tumor Type |
|---|---|---|---|---|
| Placebo | — | 1,5,9 | — | P388 |
| Vincristine | 0.8 | 1,5,9 | +114 | P388 |
| 15 | 200 | 1,5,9 | +37 | P388 |
| 15 | 100 | 1,5,9 | +18 | P388 |
| 15 | 50 | 1,5,9 | +8 | P388 |
| 06 | 200 | 1,5,9 | +47 | P388 |
| 06 | 100 | 1,5,9 | +22 | P388 |
| 06 | 50 | 1,5,9 | +16 | P388 |
| 07 | 200 | 1,5,9 | +49 | P388 |
| 07 | 100 | 1,5,9 | +29 | P388 |
| 07 | 50 | 1,5,9 | +20 | P388 |
| Placebo | — | 5,9,13 | — | COLON 26 |
| Adriamycin | 4 | 5,9,13 | +70 | COLON 26 |
| 15 | 300 | 5,9,13 | −3 | COLON 26 |
| 15 | 200 | 5,9,13 | +64 | COLON 26 |
| 15 | 100 | 5,9,13 | +15 | COLON 26 |
| 06 | 300 | 5,9,13 | +21 | COLON 26 |
| 06 | 200 | 5,9,13 | +15 | COLON 26 |
| 06 | 100 | 5,9,13 | +9 | COLON 26 |
| 07 | 300 | 5,9,13 | −58 | COLON 26 |
| 07 | 200 | 5,9,13 | −52 | COLON 26 |
| 07 | 100 | 5,9,13 | −15 | COLON 26 |

Based on the results obtained in the standard pharmacological test procedures described above, the compounds of this invention are useful as antineoplastic agents. More particularly, the compounds of this invention are useful for inhibiting the growth of neoplastic cells, causing cell death of neoplastic cells, and eradicating neoplastic cells. The compounds of this invention are therefore useful for treating solid tumors, including sarcomas and carcinomas, such as astrocytomas, prostate cancer, breast cancer, small cell lung cancer, and ovarian cancer; leukemias; lymphomas; adult T-cell leukemia/lymphoma; and other neoplastic disease states.

In addition to the utilities described above, many of the compounds of this invention are useful in the preparation of other compounds of this invention.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to this invention are prepared so that an oral dosage unit contains between about 1 and 250 mg of active compound.

The tablets, capsules and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to active ingredient, sucrose as a sweetening agent, methyl and propylparabens as preservatives, a dye and flavoring such as cherry or orange flavor.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention may also be administered directly to the airways in the form of an aerosol.

The following examples describe the preparation of representative compounds of this invention.

EXAMPLE 1

2-Iodo-11-oxo-11-H-Pyrido[2,1-b]quinazoline-6-carboxylic acid

A solution of 2-amino-5-iodobenzoic acid (25 g; 95.0 mmol), 2-chloronicotinic acid (14.97 g; 95.0 mmol), concentrated hydrochloric acid (3.17 ml; 38 mmol), and ethanol (150 ml) was heated at reflux for 18 hours, then cooled to 0° C. The precipitate was collected by filtration and the filter cake was washed with fresh ethanol (200 ml). The filter cake was dried in vacuo over phosphorous pentoxide to provide product as a yellow solid: 12.0 g.

FAB MS: m/z 367 ($M^++H$).

$^1$H NMR (DMSO.$d_6$, 300 MHz) δ 9.15 (d,1H),8.65(d, 1H), 8.57 (s, 1H), 8.26 (d, 1H), 7.75 (d, 1H), 7.28 (t,1H).

EXAMPLE 2

N-[2-(Dimethylamino)ethyl]-2-iodo-11-oxo-11H-pyrido[2,1-b1 guinazoline-6-carboxamide To a room temperature solution of 2-iodo-11-oxo-11H-pyrido[2,1-b]quinazoline-6-carboxylic acid (25 g; 62.1 mmol), N,N-dimethylethylenediamine (7.16 ml, 65.2 mmol), N,N-diisopropylethylamine (108.2 ml; 621 mmol), and dichloromethane (570 ml) was added benzotriazol-1-yloxytris(dimethethylamino)phosphonium hexafluorophosphate (35.71 g; 80.7 mmol) in one portion. After a stirring period of 18 hours, the reaction mixture was diluted with 1 N sodium hydroxide (700 ml), and extracted with dichloromethane (3×500 ml). The combined organic phases were washed with brine (700 ml), dried over anhydrous sodium sulfate, filtered and concentrated in vacuo. The residue was recrystallized repeatedly from hot methanol to provide product as a yellow solid: 19.21 g.

FAB MS: m/z 375 ($M^++H$).

$^1$H NMR(CDCl$_3$,300 MHz) 11.45 (m, 1H), 9.05 (d, 1H), 8.87 (d, 1H), 8.75 (s, 1H), 8.09 (d, 1H), 7.52 (d,1H), 7.05 (t,1H), 3.65 (q, 2H), 2.60 (t,2H), 2.41 (s, 6H).

EXAMPLE 3

2-Iodo-11-oxo-N-[2-(1-pyrrolidinyl)ethyl]-11H-pyrido[2,1-b]quinazoline-6-carboxamide To a room temperature solution of 2-iodo-11-oxo-11H-pyrido[2,1-b]quinazoline-6-carboxylic acid (2.0 g; 4.97 mmol), 1-(2-aminoethyl)pyrrolidine (1.26 ml; 9.94 mmol), N,N-diisopropylethylamine (4.33 ml; 24,8 mmol), and dichloromethane (50 ml) was added benzotriazol-1-yloxytris(dimethylamino)phosphonium hexafluorophosphate (3.3 g; 7.45 mmol) in one portion. After a stirring period of 66 hours, the reaction mixture was diluted with half-saturated sodium bicarbonate (100 ml) and extracted with dichloromethane (3×50 ml). The combined organic phases were washed with brine (70 ml), dried over anhydrous magnesium sulfate, filtered and concentrated in vacuo. The residue was purified by repeated flash chromatography. The first purification on silica gel (250 g; elution with 10% methanol/chloroform) was followed by a second purification (250 g silica gel; elution with 45% methanol/ethyl acetate followed by a gradient elution with 10–20% methanol/chloroform) to provide product as a bright lemon yellow solid: 1.82 g.

$^1$H NMR (CDCl$_3$, 300 MHz) δ 11.45 (m, 1H), 9.02 (dd, 1H), 8.84 (dd, 1H), 8.78 (d, 1H), 8.09 (dd, 1H), 7.54 (d, 1H), 7.05 (t, 1H), 3.70 (q, 2H), 2.81 (t, 2H), 2.56 (m, 4H), 1.89 (m, 4H).

EXAMPLE 4

3-Pyridinyl-boronic Acid

To −78° C. cooled n-BuLi (61 ml; 2.5 M hexane solution) was added 3-bromopyridine (20.0 g), dissolved in $Et_2O$ (−78° C.) (100 ml) by cannula during 5 minutes. After 10 minutes, a precooled (−78° C.) solution of trimethyl-borate (17.1 g) in $Et_2O$ (80 ml) was added. The reaction mixture was stirred at −78° C. for 1 hour, warmed to room temperature during 1 hour, and stirred at room temperature for ½ hour. To the reaction mixture was added 20 ml water and stirring continued. The resulting solid percipitate was collected and the supernatent concentrated to a residue. To the residue was added ethyl alcohol (100 ml) and acetic acid (8 ml) followed by heating at reflux for 35 minutes, cooling to room temperature and concentrating to dryness to give a pale yellow foamy material. The crude product was used directly in the next step.

EXAMPLE 5

4-(Tributylstannyl)pyridine

4-Bromopyridine.HCl (5.0 g) was stirred in ether (50 ml) and 5 M NaOH (5.66 ml) solution for 20 minutes. The ether layer was separated, dried over $MgSO_4$, filtered, then cooled to −78° C. The ether solution was transfered by cannula to a −78° C. solution of n-BuLi (12.34 ml). The dark brown heterogeneous solution was stirred at −78° C. for 5 minutes, prior to the dropwise addition of $n-Bu_3SnCl$. The solution became homogeneous and black/brown in color. Stirring was continued at −78° C. for 2 hours. The reaction mixture was allowed to warm to room temperature followed by stirring at room temperature for 15 minutes, diluted with water (50 ml) and extracted with ethyl acetate (3×50 ml). The combined ethyl acetate extracts were combined, washed with brine (50 ml), dried with $MgSO_4$, filtered and concentrated in vacuo to a residue. The residue was purified once on $SiO_2$ (250 g; elute with 30% ethyl acetate/hexane) to give 6.5 g of a product as a pale yellow oil. The product was used in the next step.

$^1$H NMR ($CDCl_3$,300 Mz) δ 8.52 (d, 2H), 7.40 (d, 2H), 1.54 (m, 6H), 1.37 (m, 6H), 1.12 (m, 6H), 0.90 (t, 9H). Analysis cal'c for $C_{17}H_{31}NSn$: C, 55.47%; H, 8.49%; N, 3.80%; Sn, 32.24%; Found. C, 55.08%; H, 8.57%; N, 3.67%; Sn, 32.25%.

EXAMPLE 6

N-[2-(Dimethylamino)ethyl]-11-oxo-2-(3-pyridinyl)-1H-Pyrido[2,1-b]quinazoline-6-carboxamide A mixture of N-[2-(dimethylamino)ethyl]-2-iodo-11-oxo-11H-pyrido[2,1-b]quinazoline-6-carboxamide (100 mg), 3-pyridinyl-boronic acid (225.41 mg), tetrakis(triphenylphosphine)palladium(0) (66.22 mg) and sodium carbonate (0.57 ml of 2 M (1.15 mmol)) was heated in an oil bath at 120° C.–125° C. for 45 minutes. The reaction mixture was cooled to room temperature, diluted with water (30 ml), and extracted with $CH_2Cl_2$ (3×30 ml). Combined organic phases were washed with brine (50 ml), dried with $MgSO_4$, filtered and concentrated in vacuo. The residue was purified on $SiO_2$ (50 g; gradient elution with 10–30% $MeOH/CHCl_3$) to give the desired product (66 mg).

$^1$H NMR ($CDCl_3$, 300 Mz) δ 11.49 (s, 1H), 9.03 (m, 1H), 8.99 (d, 1H), 8.85 (m, 1H), 8.43 (m, 2H), 8.14 (m, 1H), 8.03 (m, 1H), 7.96 (m, 1H), 7.48 (m, 1H), 7.04 (t, 1H), 3.71 (m, 2H), 2.62 (t, 2H), 2.46 (s, 6H).

EXAMPLE 7

N-[2-(Dimethylamino)ethyl]-11-oxo-2-(4-pyridinyl)-11H-pyrido[2,1-b]guinazoline-6-carboxamide A mixture of N-[2-(dimethylamino)ethyl]-2-iodo-11-oxo-11H-pyrido[2,1-b]quinazoline-6-carboxamide (100 mg), 4-(tributylstannyl)pyridine (126.58 mg), tetrakis (triphenylphosphine)palladium(0) (26.49 mg) and 6 ml of toluene was heated in a sealed tube at 130° C.–135° C. for 5 hours. In the middle of this time additional tetrakis (triphenylphosphine)paladium(0) (40 mg) was added. The reaction mixture was cooled to room temperature overnight. Heating was continued for 3 hours at 130–135° C. followed by cooling to room temperature, diluted with saturated $NaHCO_3$ (30 ml), and extracted with $CH_2Cl_2$ (3×30 ml). The combined $CH_2Cl_2$ extracts were washed with brine (50 ml), dried with $MgSO_4$, filtered and concentrated in vacuo to a residue which was purified on silica gel(eluted with 10–15% $MeOH/CHCl_3$) to give 44 g of the desired product as a solid.

$^1$H NMR ($CDCl_3$, 300 MHz) δ 11.48 (s, 1H), 9.09 (dd, 1H), 8.86 (dd, 1H), 8.75 m, 2H), 8.18 (dd, 1H), 7.92 (d, 1H), 7.85 (m, 1H), 7.67 (m, 2H), 7.09 (t, 1H), 3.70 (m, 2H), 2.65 (t, 2H), 2.46 (s, 6H).

EXAMPLE 8

11-Oxo-2-(4-pyridinyl)-N-[2-(1-pyrrolidinyl)ethyl]-11H-pyrido[2,1-b]guinazoline-6-carboxamide A mixture of 2-iodo-11-oxo-N-[2-(1-pyrrolidinyl)ethyl]-11H-pyrido[2,1-b]quinazoline-6-carboxamide(200 mg), 4-(tributylstannyl)pyridine (238.9 mg), tetrakis (triphenylphosphine)palladium(0) (49.99 mg) and 9 ml of toluene was heated in a sealed tube at 125° C. for 3 hours, followed by cooling to room temperature, dilution with saturated $NaHCO_3$ (30 ml), and extraction with $CH_2Cl_2$ (3×30 ml). The combined $CH_2Cl_2$ extracts were washed with brine (50 ml), dried with $MgSO_4$, filtered and concentrated in vacuo to a residue which was purified on silica gel (120 g; eluted with 10–15% $MeOH/CHCl_3$) to provide product as a yellow solid/film, 0.043 g. Electrospray MS=M/Z 414 ($M^+$+H).

$^1$H NMR ($CDCl_3$, 300 MHz) δ 11.48 (s, 1H), 9.09 (dd, 1H), 8.86 (dd, 1H), 8.75 (m, 3H), 8.18 (dd, 1H), 8.01 (d, 1H), 7.67 (m, 2H), 7.09 (t, 1H), 3.80 (m, 2H), 2.95 (t, 2H), 2.80 (m, 4H), 1.95 (m, 4H).

EXAMPLE 9

3-Quinolinylboronic acid

A solution of 3-bromoquinoline (14.6 g (0.07 mole)) in 50 ml of diethylether was added at −40° under argon to a solution of 2 M n-BuLi (37.5 ml (0.075 mole) (in cyclohexane)) in 50 ml $Et_2O$. The reaction mixture was stirred 15 minutes and 0.075 mole (7.8 g, 8.5 ml) trimethylborate was added rapidly over 2 minutes. The mixture was stirred 15 minutes at 0° C. and 4 ml of $H_2O$ was added and stirring continued for 30 minutes. The volatiles were evaporated in vacuo to a yellow tar resi-due. The residue was dissolved in 150 ml ethyl alcohol to which was added 4 ml of acetic acid and reflux-ed for 45 minutes. The volatiles were evaporated in vacuo to a yellow oily residue. The residue was stirred with 40 ml of ether to give a yellow solid which was filtered, washed with ether and dried to give 11.14 g of a solid. The solid was stirred in 100 ml of water and filtered to give 3.26 g of a solid after air drying. The crude product was used directly in the next step.

EXAMPLE 10

N-[2-(Dimethylamino)ethyl]-11-oxo-2-(3-quinolinyl)-11H-pyrido[2,1-b]quinazoline-6-carboxamide A mixture of N-[2-(dimethylamino)ethyl]-2-iodo-11-oxo-11H-pyrido[2,1-b]quinazoline-6-carboxamide (750 mg), 3-quinolinylboronic acid (743.47 mg), tetrakis-(triphenylphosphine)palladium(0) (198.67 mg) and sodium carbonate (4.3 ml of 2 M (8.6 mmol))and 33 ml of toluene was heated at 120° C. for 7 hours and cooled to room temperature. The reaction mixture was diluted with 70 ml of water and extracted with 3×70 ml $CHCl_3$. The organic layer was dried over $Na_2SO_4$ and evaporated in vacuo to a residue. The residue was purified by column chroma-tography on silica gel by elution with 5–10% $MeOH/CHCl_3$ to give 501 mg of a yellow solid.

FAB MS=M/z 438 ($M^+$+H)

$^1$H NMR($CDCl_3$,300 Mz)δ 11.50 (s, 1H), 9.30 (d, 1H), 9.08 (dd, 1H), 8.83 (dd, 1H), 8.78 (d, 1H), 8.45 (d, 1H), 8.27 (dd, 1H), 8.16 (d, 1H), 7.93 (t, 2H), 7.76 (m, 1H), 7.61 (t, 1H), 7.07 (t, 1H), 3.70 (m, 4H), 2.67 (t, 4H), 2.45 (s, 6H).

EXAMPLE 11

4-Bromo-1,2-benzenedicarboxylic acid, 2-methyl ester

4-Bromo-1,2-benzenedicarboxylic acid, 1-methyl ester

To methanol (20 ml) is added sodium hydride (1.0 g of a 60% mineral oil suspension; 25 mmol). After all solids were dissolved, the solution was added to a room temperature solution of 4-bromophthalic anydride (2.27 g; 10 mmol) dissolved in methanol (50 ml). The reaction mixture was stirred at room temperature for 10 minutes, diluted with saturated potassium carbonate solution and extracted twice with ethyl acetate. The aqueous layer was acidified to pH 1–2, then extracted with fresh ethyl acetate. The combined organic layers are dried, filtered and concentrated in vacuo to provide a mixture of benzoic acid isomers (2.21 g) as a waxy solid.

CI MS: m/z 261 ($M^+$+H).

$^1$H NMR ($CDCl_3$, 300 MHz), δ 11.05 (br s, 8.06–7.58 (m, 3H), 3.93, 3.92 (2 singlets, 3H).

EXAMPLE 12

Methyl 2-amino-4-bromo-benzoate

Methyl 2-amino-5-bromo-benzoate

To a solution of the mixture from Example 11 (2.07 g; 8 mmol), triethylamine (6.0 ml; 0.043 mol), and toluene (80 ml) was added diphenylphosphoryl azide (5.0 g; 0.018 mol) and the reaction mixture was heated at 80° C. for 2 hours. The reaction mixture was diluted with acetone (200 ml) and water (40 ml), heated further at 80° C. for 8 hours, cooled to room temperature and concentrated in vacuo. The residue was purified by flash chromatography on silica gel (elution with 15% ethyl acetate/hexane) to provide benzoic acid, 2-amino-4-bromo, methyl ester (0.514 g) as a white solid and benzoic acid, 2-amino-5-bromo, methyl ester (0.930 g) as a white solid.

Methyl 2-amino-4-bromo-benzoate

CI MS: m/z 231 ($M^+$+H).

$^1$H NMR ($CDCl_3$, 300 MHz) δ 7.71 (d, 1H), 6.84 (d, 1H), 6.74 (dd, 1H), 5.80 (br, 2H), 3.86 (s, 3H).

Methyl 2-amino-5-bromo-benzoate

CI MS: m/z 231 ($M^+$+H).

$^1$H NMR ($CDCl_3$, 300 MHz) δ 7.94 (d, 1H), 7.30 (dd, 1H), 6.57 (d, 1H), 5.78 (br, 2H), 3.85 (s, 3H).

EXAMPLE 13

3-Bromo-11-oxo-11H-pyrido[2,1-b]quinazoline-6-carboxylic acid

A solution of methyl 2-amino-4-bromo-benzoate (460 mg; 2 mmol), 2-chloronicotinic acid (315 mg; 2 mmol), concentrated hydrochloric acid (5 drops), ethanol (5 ml) and water (25 ml) was heated at reflux for 18 hours, cooled to 0° C. and filtered. The solid filter cake obtained was dried in vacuo and used directly in the next example.

EXAMPLE 14

3-Bromo-N-[2-(dimethylamino)ethyl]-11-oxo-11H-pyrido[2,1-b]quinazoline-6-carboxamide The 3-bromo-11-oxo-11H-pyrido[2,1-b]quina-zoline-6-carboxylic acid was dissolved in dichloromethane (25 ml). To the reaction mixture was added N,N-dimethyl-ethylenediamine (1 g; 0.0023 mol), followed by the BOP reagent (1 g, 0.0023 mol). The reaction mixture was stirred at room temperature for 30 minutes, diluted with water and extracted with dichloromethane. The combined organic phases were dried, filtered and concentrated in vacuo. The residue was purified by flash chromatography on silica gel (elution with 10% methanol/chloroform) to provide product as a yellow solid: 0.338 g.

CI MS: m/z 391 ($M^+$+H).

$^1$H NMR ($CDCl_3$, 300 MHz) δ 9.04 (d, 1H), 8.84 (d, 1H), 8.27 (d, 1H), 8.03 (s, 1H), 7.60 (d, 1H), 7.09 (t, 1H), 3.67 (q, 2H), 2.62 (m, 2H), 2.41 (s, 6H).

EXAMPLE 15

N-[2-(Dimethylamino)ethyl]-11-oxo-3-(3-pyridinyl)-11H-pyrido[2,1-b]quinazoline-6-carboxamide The procedure of Example 6 was used with the product of Example 14 (39 mg, 0.1 mmol), product of Example 4 (123 mg, 1.0 mmol), tetrakis(triphenylphospine)palladium(0) (29 mg, 0.025 mmol), 2 M sodium carbonate solution (0.5 ml, 1.0 mmol), and toluene (5 ml).

Yield: 6.0 mg yellow solid.

CI MS: m/z 388 ($M^+$+H).

$^1$H NMR ($CDCl_3$) δ 11.57 (br s, 1H), 9.08 (dd, 1H), 9.02 (d, 1H), 8.84 (dd, 1H), 8.73 (dd, 1H), 8.54 (d, 1H), 8.03 (m, 2H), 7.75 (dd, 1H), 7.49 (m, 1H), 7.05 (t, 1H), 3.73 (m, 2H), 2.62 (t, 2H), 2.46 (s, 6H).

EXAMPLE 16

N-[2-(Dimethylamino)ethyl]-11-oxo-3-(4-pyridinyl)-11H-pyrido[2,1-b]quinazoline-6-carboxamide The procedure of Example 7 was used with the product of Example 14 (39 mg, 0.1 mmol), product of Example 5 (55 mg, 0.15 mmol), tetrakis(triphenylphosphine)palladium(0) (23 mg, 0.0020 mmol), and toluene (2 ml).

Yield: 11.0 mg yellow solid.

CI MS: m/z 388 ($M^+$+H).

$^1$H NMR (CDCl$_3$) δ 11.53 (br s, 1H), 9.07 (dd, 1H), 8.86 (dd, 1H), 8.80 m, 2H), 8.55 (d, 1H), 8.05 (dd, 1H), 7.76 (d, 1H), 7.67 (m, 2H), 7.05 (t, 1H), 3.73 (m, 2H), 2.62 (t, 2H), 2.46 (s, 6H).

We claim:

1. A compound having the formula

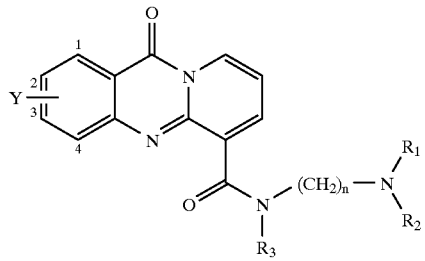

wherein:
(A) n=2–4;
(B) R$_1$ and R$_2$ are the same or different and selected from the group consisting of H, (C–C$_3$) alkyl, —CH$_2$CH$_2$OH, —CH$_2$CH$_2$NH$_2$, and —CH$_2$CH$_2$N(CH$_3$)$_2$ or R$_1$ and R$_2$ are alkyl moieties which are taken together to form a 4- to 7- membered ring;
(C) R$_3$ is selected from the group consisting of H, —CH$_3$, —CH$_2$CH$_3$, and —CH$_2$CH$_2$NH$_2$;
(D) Y is located at the 2- or 3- position of the pyridoquinazolinone nucleus and is a radical selected from the group consisting of 3-pyridinyl, 4-pyridinyl, and 3-quinolinyl;
R$_4$ is H or (C$_1$–C$_4$) straight-chain alkyl;
R$_5$ and R$_6$ are the same or different and are selected from the group consisting of H, (C$_1$–C$_4$) straight-chain alkyl, —CH$_2$CH$_2$OH, —CH$_2$CH$_2$NH$_2$, and —CH$_2$CH$_2$N(CH$_3$)$_2$, or R$_5$ and R$_6$ are alkyl moieties which are taken together to form a 4–7 membered ring;
or a pharmaceutically acceptable salt thereof.

2. A compound according to claim 1, having the formula:

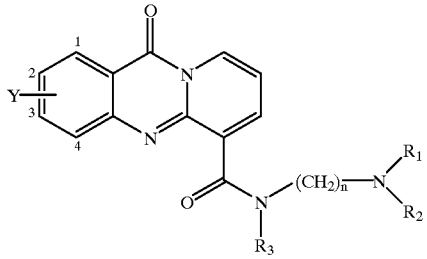

wherein:
(A) n=2;
(B) R$_1$ and R$_2$ are both —CH$_3$, or R$_1$ and R$_2$ are alkyl moieties which are taken together to form a pyrrolidine ring;
(C) R$_3$ is H;
(D) Y is selected from the group consisting of 3-pyridinyl, 4-pyridinyl, and 3-quinolinyl;
or a pharmaceutically acceptable salt thereof.

3. The compound according to claim 2, which is N-[2-(dimethylamino)ethyl]-11-oxo-2-(3-pyridinyl)-11H-pyrido[2,1-b]quinazoline-6-carboxamide or a pharmaceutically acceptable salt thereof.

4. The compound according to claim 1, which is N-[2-(dimethylamino)ethyl]-11-oxo-2-(4-pyridinyl)-11H-pyrido[2,1-b]quinazoline-6-carboxamide
or a pharmaceutically acceptable salt thereof.

5. The compound according to claim 1, which is 11-oxo-2-(4-pyridinyl)-N-[2-(1-pyrrolidinyl)ethyl]-11H-pyrido[2,1-b]quinazoline-6-carboxamide or a pharmaceutically acceptable salt thereof.

6. The compound according to claim 1, which is N-[2-(dimethylamino)ethyl]-11-oxo-2-(3-quinolinyl)-11H-pyrido[2,1-b]quinazoline-6-carboxamide or a pharmaceutically acceptable salt thereof.

7. The compound according to claim 1, which is N-[2-(dimethylamino)ethyl]-11-oxo-3-(3-pyridinyl)-11H-pyrido[2,1-b]quinazoline-6-carboxamide or a pharmaceutically acceptable salt thereof.

8. The compound according to claim 1, which is N-[2-(dimethylamino)ethyl]-11-oxo-3-(4-pyridinyl)-11H-pyrido[2,1-b]quinazoline-6-carboxamide or a pharmaceutically acceptable salt thereof.

9. A pharmaceutical composition which comprises a compound having the formula:

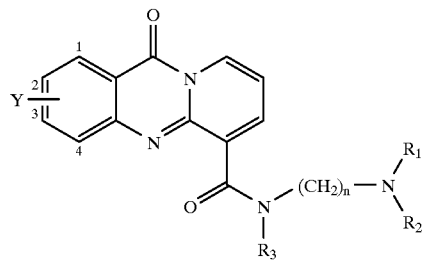

wherein:
(A) n=2–4;
(B) R$_1$ and R$_2$ are the same or different and selected from the group consisting of H, (C$_1$–C$_3$) alkyl, —CH$_2$CH$_2$OH, —CH$_2$CH$_2$NH$_2$, and —CH$_2$CH$_2$N(CH$_3$)$_2$ or R$_1$ and R$_2$ are alkyl moieties which are taken together to form a 4- to 7- membered ring;
(C) R$_3$ is selected from the group consisting of H, —CH$_3$, —CH$_2$CH$_3$, and —CH$_2$CH$_2$NH$_2$;
(D) Y is located at the 2- or 3- position of the pyridoquinazolinone nucleus and is a radical selected from the group consisting of 3-pyridinyl, 4-pyridinyl, and 3-quinolinyl;
R$_4$ is H or (C$_1$–C$_4$) straight-chain alkyl;
R$_5$ and R$_6$ are the same or different and are selected from the group consisting of H, (C$_1$–C$_4$) straight-chain alkyl, —CH$_2$CH$_2$OH, —CH$_2$CH$_2$NH$_2$, and —CH$_2$CH$_2$N(CH$_3$)$_2$, or R$_5$ and R$_6$ are alkyl moieties which are taken together to form a 4–7 membered ring;
or a pharmaceutically acceptable salt thereof and a pharmaceutical carrier.

10. A method of inhibiting growth of colon cancer in a mammal in need thereof which comprises administering to said mammal an effective amount of a compound having the formula

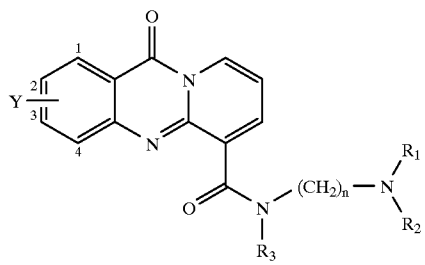

wherein:

(A) n=2–4;

(B) $R_1$ and $R_2$ are the same or different and selected from the group consisting of H, ($C_1$–$C_3$) alkyl, —$CH_2CH_2OH$, —$CH_2CH_2NH_2$, and —$CH_2CH_2N(CH_3)_2$ or $R_1$ and $R_2$ are alkyl moieties which are taken together to form a 4- to 7- membered ring;

(C) $R_3$ is selected from the group consisting of H, —$CH_3$, —$CH_2CH_3$, and —$CH_2CH_2NH_2$;

(D) Y is located at the 2- or 3- position of the pyridoquinazolinone nucleus and is a radical selected from the group consisting of 3-pyridinyl, 4-pyridinyl, and 3-quinolinyl;

$R_4$ is H or (C–$C_4$) straight-chain alkyl;

$R_5$ and $R_6$ are the same or different and are selected from the group consisting of H, ($C_1$–$C_4$) straight-chain alkyl, —$CH_2CH_2OH$, —$CH_2CH_2NH_2$, and —$CH_2CH_2N(CH_3)_2$, or $R_5$ and $R_6$ are alkyl moieties which are taken together to form a 4–7 membered ring;

or a pharmaceutically acceptable salt thereof.

11. A method of inhibiting growth of leukemia cells in a mammal in need thereof which comprises administering to said mammal an effective amount of a compound having the formula

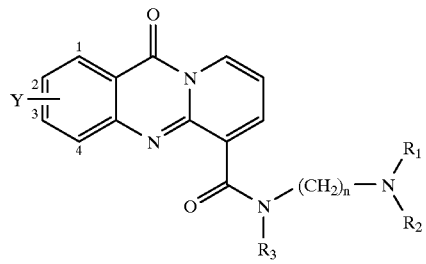

wherein:

(A) n=2–4;

(B) $R_1$ and $R_2$ are the same or different and selected from the group consisting of H, ($C_1$–$C_3$) alkyl, —$CH_2CH_2OH$, —$CH_2CH_2NH_2$, and —$CH_2CH_2N(CH_3)_2$ or $R_1$ and $R_2$ are alkyl moieties which are taken together to form a 4- to 7- membered ring;

(C) $R_3$ is selected from the group consisting of H, —$CH_3$, —$CH_2CH_3$, and —$CH_2CH_2NH_2$;

(D) Y is located at the 2- or 3- position of the pyridoquinazolinone nucleus and is a radical selected from the group consisting of 3-pyridinyl, 4-pyridinyl, and 3-quinolinyl;

$R_4$ is H or ($C_1$–$C_4$) straight-chain alkyl;

$R_5$ and $R_6$ are the same or different and are selected from the group consisting of H, ($C_1$–$C_4$) straight-chain alkyl, —$CH_2CH_2OH$, —$CH_2CH_2NH_2$, and —$CH_2CH_2N(CH_3)_2$, or $R_5$ and $R_6$ are alkyl moieties which are taken together to form a 4–7 membered ring;

or a pharmaceutically acceptable salt thereof.

* * * * *